(12) United States Patent
Griffiths et al.

(10) Patent No.: US 11,918,407 B2
(45) Date of Patent: Mar. 5, 2024

(54) FLEXIBLE DOSE ESTIMATION WITH USER-DEFINED VOLUMES

(71) Applicant: BAYER HEALTHCARE LLC, Whippany, NJ (US)

(72) Inventors: David Griffiths, Pittsburgh, PA (US); Arthur Uber, Pittsburgh, PA (US); Jacob Agris, Great Neck Estates, NY (US); Ting Lu, Hoboken, NJ (US); Peter Thompson, Toronto (CA)

(73) Assignee: BAYER HEALTHCARE LLC, Whippany, NJ (US)

( * ) Notice: Subject to any disclaimer, the term of this patent is extended or adjusted under 35 U.S.C. 154(b) by 802 days.

(21) Appl. No.: 17/044,048

(22) PCT Filed: Apr. 8, 2019

(86) PCT No.: PCT/US2019/026280
§ 371 (c)(1),
(2) Date: Sep. 30, 2020

(87) PCT Pub. No.: WO2019/199644
PCT Pub. Date: Oct. 17, 2019

(65) Prior Publication Data
US 2021/0361253 A1    Nov. 25, 2021

Related U.S. Application Data
(60) Provisional application No. 62/655,373, filed on Apr. 10, 2018.

(51) Int. Cl.
*A61B 6/00* (2006.01)
*A61B 6/03* (2006.01)
(Continued)

(52) U.S. Cl.
CPC .............. *A61B 6/581* (2013.01); *A61B 6/032* (2013.01); *G16H 10/60* (2018.01); *G16H 20/40* (2018.01); *G16H 50/50* (2018.01)

(58) Field of Classification Search
None
See application file for complete search history.

(56) References Cited

U.S. PATENT DOCUMENTS

| 8,953,861 B2 | 2/2015 | Couch et al. |
| 8,958,617 B2 | 2/2015 | Couch et al. |
| (Continued) | | |

FOREIGN PATENT DOCUMENTS

| CN | 106228884 A | * | 12/2016 | ............. G09B 23/28 |
| CN | 110139607 A | * | 8/2019 | ............. A61B 5/055 |
| (Continued) | | | | |

OTHER PUBLICATIONS

Christ; et al, "The Virtual Family—development of surface-based anatomical models of two adults and two children for dosimetric simulations", Phys. Med. Biol., 2010, 55, N23-N38.
(Continued)

*Primary Examiner* — Mohammed Rachedine
(74) *Attorney, Agent, or Firm* — James R. Stevenson; Bryan P. Clark

(57) ABSTRACT

Described is a method of providing an estimate of radiation dose received by a patient during an imaging scan performed by an imaging system. The method includes receiving patient information about the patient, receiving scan data generated during the imaging scan of the patient by the imaging system, creating a virtual dose model of the patient based upon the patient information and the scan data, receiving a selection of a region of interest of the patient, performing a dose simulation on the virtual dose model of the patient or a portion thereof, and determining, based upon
(Continued)

an outcome of the dose simulation, an estimate of the radiation dose received within the region of interest. The imaging scan can be a partial imaging scan of a portion of the patient. Also provided is a system and software for carrying out this method.

25 Claims, 3 Drawing Sheets

(51) Int. Cl.
*A61N 5/10* (2006.01)
*G16H 10/60* (2018.01)
*G16H 20/40* (2018.01)
*G16H 50/50* (2018.01)

(56) References Cited

U.S. PATENT DOCUMENTS

| | | | |
|---|---|---|---|
| 9,547,893 B2 | 1/2017 | Couch et al. | |
| 9,792,680 B2 | 10/2017 | Couch et al. | |
| 10,438,348 B2 | 10/2019 | Couch et al. | |
| 10,546,375 B2 | 1/2020 | Couch et al. | |
| 2005/0209888 A1 | 9/2005 | Oowaki et al. | |
| 2006/0098856 A1 | 5/2006 | Botterweck et al. | |
| 2007/0053480 A1 | 3/2007 | Nishide et al. | |
| 2011/0110573 A1 | 5/2011 | Wiegert et al. | |
| 2016/0278719 A1* | 9/2016 | Jensen | A61B 6/4441 |
| 2017/0123074 A1 | 5/2017 | Couch et al. | |
| 2017/0202534 A1 | 7/2017 | Crotty et al. | |
| 2017/0215818 A1* | 8/2017 | De Man | A61B 6/5205 |
| 2017/0228860 A1 | 8/2017 | Couch et al. | |
| 2017/0243350 A1 | 8/2017 | Couch et al. | |
| 2017/0245825 A1 | 8/2017 | Star-Lack et al. | |
| 2019/0274641 A1* | 9/2019 | Joskowicz | G06T 11/006 |
| 2019/0274653 A1* | 9/2019 | Guo | A61B 6/032 |

FOREIGN PATENT DOCUMENTS

| | | | | |
|---|---|---|---|---|
| JP | 2007175323 A | 7/2007 | | |
| JP | 2012055510 A | 3/2012 | | |
| JP | 2014236798 A | 12/2014 | | |
| WO | 2012075577 A1 | 6/2012 | | |
| WO | WO-2017053869 A1 * | 3/2017 | | A61B 6/027 |
| WO | WO-2017194787 A1 * | 11/2017 | | G06T 5/002 |
| WO | 2018156803 A1 | 8/2018 | | |

OTHER PUBLICATIONS

"International Preliminary Report on Patentability from PCT Application No. PCT/US2019/026280", dated Oct. 22, 2020.

Karmer; et al, "All about MAX: a mail adult voxel phantom for Monte Carlo calculations in radiation protection dosimetry", Phys. Med. Biol., 2003, 48, 1239-1262.

Na Yong Hum; et al, "Deformable adult human phantoms for radiation protection dosimetry: anthropometric data representing size distributions of adult worker populations and software algorithms", Phys Med Biol., Jul. 7, 2010, 3789-3811.

Perisinakis; et al, "The effect of iodine uptake on radiation dose absorbed by patient tissues in contrast enhanced CT imaging: Implications for CT dosimetry", Eur. Radiol., Jul. 14, 2017.

Segars W.P.; et al, "4D XCAT phantom for multimodality imaging research", Medical Physics, Sep. 2010, vol. 37 No 9, 4902-4915.

Bardo; et al, "Comparison of Patient-Specific & Reference-Phantom Methods for CT Dose Estimation in the Pediatric Population", 2012.

* cited by examiner

FLEXIBLE DOSE ESTIMATION WITH USER-DEFINED VOLUMES

CROSS-REFERENCE TO RELATED APPLICATION

This application is a U.S. national phase application under 35 U.S.C. § 371 of International Application No. PCT/US2019/026280, filed Apr. 8, 2019 and claims priority to U.S. Provisional Patent Application No. 62/655,373, filed Apr. 10, 2018, the disclosures of which are hereby incorporated by reference in their entirety.

BACKGROUND

Field of the Invention

Embodiments of this disclosure are generally directed to systems and methods for dose estimation in the field of healthcare imaging, such as systems and methods that estimate dose using more accurate patient models.

Description of Related Art

Patient imaging is an indispensable diagnostic tool that is widely used in hospitals and medical facilities around the world. Patient imaging can involve the use of radiation-based modalities, such as computed tomography (CT), radiographic fluoroscopy (R/F), real-time angiography, positron emission tomography combined with computed tomography (PET/CT), single-photon emission computed tomography (SPECT), among others, as well as modalities that do not use ionizing radiation, such as ultrasounds and magnetic resonance imaging (MRI). What all of these modalities have in common, is that, in order to capture patient images, the patient is exposed to a dose of energy. Whether it be ionizing radiation, such as in the case of CT, or heat input (SAR—Specific Absorption Rate), as in the case of MRI, there may be undesirable side effects of such exposure. For example, according to the International Atomic Energy Agency (IAEA), a chest or abdomen CT scan exposes the patient to 5 to 20 mSv as opposed to less than 0.1 mSv in an ordinary chest x-ray. It has also been reported that a spine CT scan exposes a patient to approximately 1.5-10 mSv as opposed to 1.5 mSv in an ordinary spine x-ray. A whole body CT may expose the patient to more than 20 mSv. Unfortunately, lowering the exposure in a CT scan has a detrimental effect on the quality of the acquired CT images, which in turn can negatively affect the diagnosis. The rise in the awareness of the harms of exposure to excessive x-ray radiation in CT scans in recent years has resulted in a great focus on the As Low As Reasonably Achievable ("ALARA") principle and has stimulated significant interest in ways to optimize CT imaging and monitor dose exposure. Currently, systems and methods of estimating exposure and monitoring radiation dose are available and widely used. One of the most prominent such uses is through the Radimetrics™ Enterprise Platform available from Bayer HealthCare LLC. However, these currently available dose estimation techniques often use radiation phantoms that over-simplify the size, shape, and composition of a human body, resulting in less than ideal dose estimations.

Other existing techniques for estimating dose distributions tend to focus on radiation therapy applications, rather than estimating the dose received through diagnostic imaging procedures. For example, the ImpactMC CT dosimetry software program (http://www.ct-imaging.de/en/ct-software-e/impactmce.html) generates axial images and provides dose maps based on the pixels in the axial images. However, this program does not give proper consideration to the human anatomy. For instance, it does not construct human anatomy out of the acquired images, fill in portions of the body for which no axial images were obtained, allow for the morphing of a base phantom, provide organ segmentation, or estimate organ dose exposure. By way of further example, VirtualDose™ CT, a virtual dose model from Virtual Phantoms, Inc., enables radiation dose calculations through deformable 3D/4D patient anatomical modeling and radiation dose calculations using the Monte Carlo methods. However, this product only provides average organ dose for a pre-determined list of organs, does not provide dose maps, and does not allow users to obtain dose information from a selected region of interest. Further, this product estimates dose for a set of pre-constructed phantoms. Similarly, Segers, W. P. et al., "4D XCAT phantom for multimodality imaging research," Med. Phys. 37(9):4902-15, September 2010, describes a 4D virtual phantom model based on anatomies from segmentation of the Visible Male and Female anatomical datasets from the National Library of Medicine as well as patient datasets using a set of pre-constructed phantoms. However, Segers does not provide dose estimation on an individualized patient basis or allow for dose estimation of a selectable region of interest.

SUMMARY

An object of certain embodiments of this disclosure is to provide approaches for estimating patient energy exposure during patient imaging. As will become apparent in the following paragraphs, the embodiments described herein relate to systems and methods for dose estimation using more accurate patient models. The dose estimation system provides a system for creating a virtual dose model based on scan data from a partial scan of the patient as well as patient information and can be used to estimate the radiation dose or exposure delivered to patients from a variety of modalities. Various aspects of the present disclosure may be further characterized by one or more of the following clauses:

Clause 1: A system, comprising: a dose simulator in communication with an imaging system, the dose simulator comprising a user interface, a processor, and a non-transitory storage medium comprising programming instructions, wherein the programming instructions, if executed, enable the processor to cause the dose simulator to: receive patient information about the patient, wherein the patient information comprises information about one or more physical characteristics of the patient; receive scan data, wherein the scan data is generated during an imaging scan of the patient by the imaging system, wherein the imaging scan is a partial imaging scan of a portion of the patient, and wherein the scan data represents partial scan data covering the portion of the patient; create a virtual dose model of the patient based upon the patient information and the partial scan data; receive a selection of a region of interest of the patient; perform a dose simulation on the virtual dose model of the patient or a portion thereof; and determine, based upon an outcome of the dose simulation, an estimate of the radiation dose received within the region of interest.

Clause 2: The system of clause 1, wherein the programming instructions, if executed, further enable the processor to present the estimate of the radiation dose received within the region of interest in a visually perceptible form on the display screen.

Clause 3: The system of clause 1, wherein the patient information comprises at least one of the patient's height, body size, body weight, and body shape.

Clause 4: The system of clause 1, further comprising a peripheral device, wherein at least a portion of the patient information is received from the peripheral device.

Clause 5: The system of clause 4, wherein the peripheral device is selected from the group consisting of a body scanner, camera, scale, and contrast injector.

Clause 6: The system of clause 1, wherein the virtual dose model comprises a plurality of voxels, wherein a material or tissue type is assigned to each of the plurality of voxels.

Clause 7: The system of clause 1, wherein the virtual dose model is a full body model of the patient.

Clause 8: The system of clause 1, wherein the dose simulation is performed on the virtual dose model through the use of a Monte Carlo simulation technique.

Clause 9: The system of clause 1, wherein the imaging system is a computed tomography system and the imaging scan is a computed tomography scan.

Clause 10: Dose simulator software stored on a non-transitory storage medium to providing an estimate of radiation dose received by a patient during an imaging scan performed by an imaging system, the software comprising programming instructions that, if executed, enable a processor to cause the dose simulator software to: receive patient information about the patient, wherein the patient information comprises information about one or more physical characteristics of the patient; receive scan data, wherein the scan data is generated during an imaging scan of the patient by the imaging system, wherein the imaging scan is a partial imaging scan of a portion of the patient, and wherein the scan data represents partial scan data covering the portion of the patient; create a virtual dose model of the patient based upon the patient information and the partial scan data; receive a selection of a region of interest of the patient; perform a dose simulation on the virtual dose model of the patient or a portion thereof; and determine, based upon an outcome of the dose simulation, an estimate of the radiation dose received within the region of interest.

Clause 11: The dose simulator software of clause 10, wherein the programming instructions, if executed, further enable the processor to present the estimate of the radiation dose received within the region of interest in a visually perceptible form.

Clause 12: The dose simulator software of clause 10, wherein the patient information comprises at least one of the patient's height, body size, body weight, and body shape.

Clause 13: The dose simulator software of clause 10, wherein at least a portion of the patient information is received from a peripheral device.

Clause 14: The dose simulator software of clause 10, wherein the peripheral device is selected from the group consisting of a body scanner, camera, scale, and contrast injector.

Clause 15: The dose simulator software of clause 10, wherein the virtual dose model comprises a plurality of voxels, wherein a material or tissue type is assigned to each of the plurality of voxels.

Clause 16: The dose simulator software of clause 10, wherein the virtual dose model is a full body model of the patient.

Clause 17: The dose simulator software of clause 10, wherein the dose simulation is performed on the virtual dose model through the use of a Monte Carlo simulation technique.

Clause 18: The dose simulator software of clause 10, wherein the imaging system is a computed tomography system and the imaging scan is a computed tomography scan.

Clause 19: A method of creating a virtual dose model of a patient that can be used to provide an estimate of radiation dose received by the patient during an imaging scan performed by an imaging system, comprising: receiving patient information about the patient, wherein the patient information comprises information about one or more physical characteristics of the patient; receiving scan data, wherein the scan data is generated during the imaging scan of the patient by the imaging system, wherein the imaging scan is a partial imaging scan of a portion of the patient, and wherein the scan data represents partial scan data covering the portion of the patient; extracting, from the scan data, a Hounsfield value attributed to each of a plurality of voxels; assigning a material or tissue type to each of the plurality of voxels; determining a plurality of voxels for which no scan data is available; and assigning a material or tissue type to each of the plurality of voxels for which no scan data is available by using the patient information to estimate the material or tissue type in the voxels for which no scan data is available.

Clause 20: The method of clause 19, wherein assigning the material or tissue type to each of the plurality of voxels comprises, for each of at least a portion of the plurality of voxels, extracting from the scan data a Hounsfield value attributed to the voxel and comparing the Hounsfield value of the voxel to correlation data representing a known relationship between Hounsfield values and types of materials or tissues.

Clause 21: The method of clause 20, wherein the correlation data is stored in a database.

Clause 22: The method of clause 19, wherein assigning the material or tissue type to each of the plurality of voxels comprises accounting for a presence of a contrast agent in one or more of the voxels.

Clause 23: The method of clause 19, wherein assigning a material or tissue type to each of the plurality of voxels for which no scan data is available further comprises accessing a phantom database and referencing a tissue or material type in a corresponding voxel of a phantom selected from the phantom database.

Clause 24: The method of clause 23, wherein the phantom selected from the phantom database is selected based upon a comparison of the patient information with characteristics of the phantom.

Clause 25: A method of providing an estimate of radiation dose received by a patient during an imaging scan performed by an imaging system, comprising: receiving patient information about the patient, wherein the patient information comprises information about one or more physical characteristics of the patient; receiving scan data, wherein the scan data is generated during the imaging scan of the patient by the imaging system, wherein the imaging scan is a partial imaging scan of a portion of the patient, and wherein the scan data represents partial scan data covering the portion of the patient; creating a virtual dose model of the patient based upon the patient information and the partial scan data; receiving a selection of a region of interest of the patient; performing a dose simulation on the virtual dose model of the patient or a portion thereof; and determining, based upon an outcome of the dose simulation, an estimate of the radiation dose received within the region of interest.

Clause 26: The method of clause 25, further comprising presenting the estimate of the radiation dose received within the region of interest in a visually perceptible form.

Clause 27: The method of clause 26, wherein the visually perceptible form comprises at least one of a display on a display screen and a printed report.

Clause 28: The method of clause 25, wherein the patient information comprises at least one of the patient's height, body size, body weight, and body shape.

Clause 29: The method of clause 25, wherein at least a portion of the patient information is received from a peripheral device.

Clause 30: The method of clause 29, wherein the peripheral device is selected from the group consisting of a body scanner, camera, scale, and contrast injector.

Clause 31: The method of clause 25, wherein the patient information further comprises information about the imaging scan performed by the imaging system.

Clause 32: The method of clause 25, wherein the virtual dose model comprises a plurality of voxels, and wherein creating a virtual dose model comprises assigning a material or tissue type to each of the plurality of voxels.

Clause 33: The method of clause 32, wherein assigning the material or tissue type to each of the plurality of voxels comprises, for each of at least a portion of the plurality of voxels, extracting from the scan data a Hounsfield value attributed to the voxel and comparing the Hounsfield value of the voxel to correlation data representing a known relationship between Hounsfield values and types of materials or tissues.

Clause 34: The method of clause 33, wherein the correlation data is stored in a database.

Clause 35: The method of clause 33, wherein assigning the material or tissue type to each of the plurality of voxels comprises accounting a presence of a contrast agent in one or more of the voxels.

Clause 36: The method of clause 25, wherein the virtual dose model is a full body model of the patient.

Clause 37: The method of clause 36, wherein creating the virtual dose model comprises determining a plurality of voxels for which no scan data is available and assigning a material or tissue type to each of the plurality of voxels for which no scan data is available by using the patient information to estimate the material or tissue type in the plurality of voxels for which no scan data is available.

Clause 38: The method of clause 37, wherein assigning a material or tissue type to each of the plurality of voxels for which no scan data is available further comprises accessing a phantom database and referencing a tissue or material type in a corresponding voxel of a phantom selected from the phantom database.

Clause 39: The method of clause 38, wherein the phantom selected from the phantom database is selected based upon a comparison of the patient information with characteristics of the phantom.

Clause 40: The method of clause 25, wherein performing the dose simulation on the virtual dose model comprises the use of a Monte Carlo simulation technique.

Clause 41: The method of clause 25, wherein the imaging system is a computed tomography system and the imaging scan is a computed tomography scan.

Clause 42: The method of clause 25, further comprising: obtaining information of a location, size, and position of one or more objects other than the patient; and updating the dose simulation of the virtual dose model to account for radiation scattered from the one or more objects other than the patient.

Clause 43: The method of clause 42, wherein the one or more other objects are selected from the group consisting of medical equipment and a person other than the patient.

DETAILED DESCRIPTION

Figure 1:
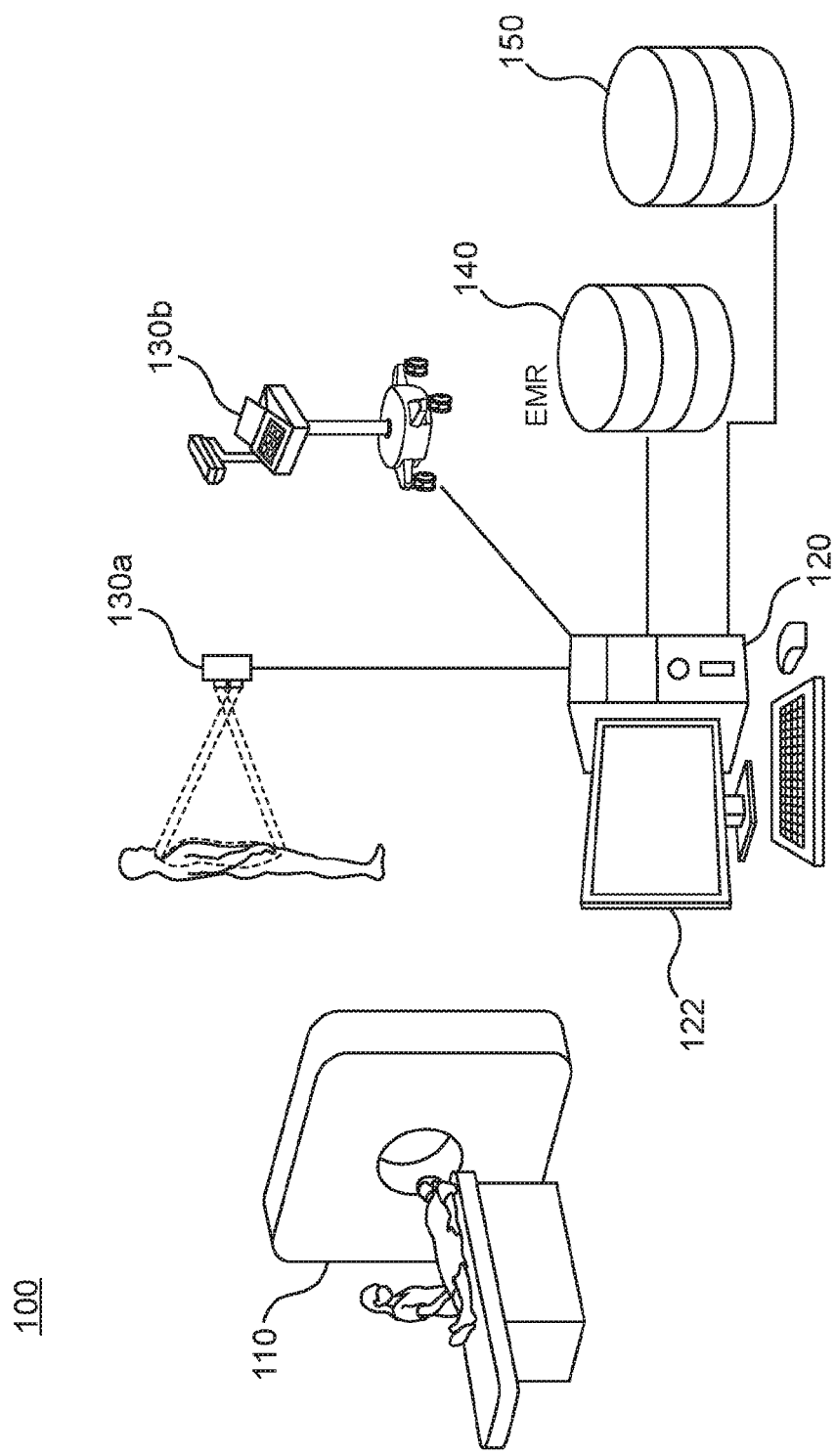
FIG. 1 illustrates a scanning environment and related computing systems according to one non-limiting embodiment of the present disclosure.

For purposes of the description hereinafter, spatial orientation terms shall relate to the embodiment as it is oriented in the drawing figures. However, it is to be understood that the various embodiments of this disclosure may assume alternative variations and step sequences, except where expressly specified to the contrary. It is also to be understood that the specific devices and processes illustrated in the attached drawings, and described in the following specification, are simply exemplary. Hence, specific dimensions and other physical characteristics related to the embodiments disclosed herein are not to be considered as limiting.

As used in the specification, the singular form of "a", "an", and "the" include plural referents unless the context clearly dictates otherwise.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

All documents, such as but not limited to issued patents and patent applications, referred to herein, and unless otherwise indicated, are to be considered to be "incorporated by reference" in their entirety.

Embodiments of the disclosure are generally directed to approaches for estimating patient radiation exposure during patient imaging. More specifically, embodiments of the disclosure provide efficient approaches for generating a suitable patient model used to make such an estimate. As described in detail below, the dose estimation system provides a system for creating a virtual dose model that can be used to estimate the radiation dose or exposure delivered to patients from a variety of modalities, such as CT, real-time angiography, PET/CT, SPECT, etc. For modalities that do not utilize ionizing radiation, the system and related software could compute other quantities of interest, such as heat input for ultrasound or MRI. Embodiments of this disclosure can provide improved radiation dose modeling and management during diagnostic imaging and radiation therapy procedures. These embodiments allow, for example, for a patient-specific dose model to be generated using only a partial scan of the patient, and consequently using less dose than a full body scan to generate the model. As will be described, generation of the patient-specific dose model, including a full body model, is achieved through a unique and non-conventional approach that represents an improvement in the field of radiation dose estimation and management by allowing for a more robust and complete picture of the total dose exposure of a patient while using less radiation exposure to obtain this information. For example, embodiments of this disclosure allow for a flexible and patient-specific radiation dose model that accounts for actual patient shape and size and uses measured and estimated tissue composition within different voxels of the patient, which can lead to increased accuracy over conventional generalized dose models that are based on generic shapes (cylinders, blocks) or scaled versions of a generic patient with a different body shape. Non-limiting embodiments or aspects of the disclosure allow for dose estimation and management to be achieved during diagnostic imaging and radiation therapy procedures in a more accurate and efficient manner, while also using less radiation to obtain the information required to make these predictions.

FIG. 1 illustrates an example of a scanning environment 100 and related computing systems configured to provide a dose estimate, according to one embodiment of the disclosure. As shown, the scanning environment 100 includes an imaging system 110, a dose simulator 120, a peripheral device 130, which in this example is in the form of a body scanner, and an information database 140, which in this example is an electronic medical record (EMR) database.

The imaging system 110 can be any of various known imaging modalities capable of capturing a medical image of a patient. Examples include imaging modalities that deliver ionizing radiation, such as CT scanners, real-time angiography, PET/CT, SPECT, as well as imaging modalities that deliver doses of energy in forms other than ionizing radiation, such as heat inputs. Exemplary modalities in this latter group include ultrasound and MM. At various points throughout this disclosure, "dose" is discussed in terms of "radiation dose," such as the ionizing radiation dose delivered to a patient during, for example, CT imaging. However, the disclosure is not so limited, and the "dose" may instead refer to "energy dose" when used with a modality, such as MRI, that does not use ionizing radiation.

In one non-limiting embodiment, dose simulator 120 comprises a computing system and software application(s) configured to generate a patient-specific virtual radiation dose model and, using this model, provide a simulated estimate of the dose delivered to a patient by the imaging system 110. Dose simulator 120 can include at least a processor and software instructions stored in non-transitory machine-readable media that, when executed, enable the processor to perform the methods discussed herein. Dose simulator 120 may also include one or more hardware components, such as a user interface for entering commands in the form of, for example, a keyboard, mouse, touchscreen, or wired or wireless device (e.g., a smartphone, laptop, remote control, or PDA) in communication with dose simulator 120. Dose simulator 120 can also include or be associated with a display 122 (which may be a touchscreen) that is capable of displaying various images and information, as discussed herein, or otherwise presenting such information in a visually perceptible form, as well as a printer for generating a printed report.

In order to generate a patient-specific virtual radiation dose model and use this model to provide a simulated estimate of the dose that would be delivered to a patient by imaging system 110, dose simulator 120 can first receive information about the subject patient and information about the imaging procedure to be performed by imaging system 110 on the subject patient. This information is collectively referred to herein as "patient information." Dose simulator 120 can receive this patient information from various sources.

For example, dose simulator 120 can be in communication with imaging system 110 to receive information from imaging system 110, including information about imaging system 110 itself. This imaging system information can include parameters and operational details concerning how the imaging system performs a scan operation to generate raw data (including the scan parameters such as timing and tube voltage), how the scanner collects the raw data (including how the detector array functions), and how the scanner generates images from the raw data (including how the raw data is reconstructed into an image).

Dose simulator 120 can also receive information about a subject patient, such as physical characteristics of the subject patient from, for example, the Hospital Information System (HIS), Electronic Medical Record (EMR) database, the Radiology Information System (RIS), the Laboratory Information System (LIS), or another information database 140 within or available to the imaging facility. Examples of such characteristics include the patient's age, height, body size, sex, weight, body mass index (BMI), body shape, body surface area (BSA), bone mass measurement (BMM), or other biometric data that can be used to measure or project an approximation of patient geometry. This information may also be entered by a user directly into dose simulator 120 through the user interface thereof. This information may also include medical history of the patient, including information indicative of genetic conditions of the patient, information related to the patient's previous radiation exposure, and other information that may be usable to accomplish the goals of the present disclosure. In certain non-limiting embodiments, information on the tissue and/or bone density of the subject patient may be useful to approximate the radiation dose distribution. For example, a patient diagnosed with osteoporosis would have a lower bone density which could affect the attenuation of the x-ray beam as it passes through the patient. In another non-limiting embodiment, details such as a pacemaker and metallic or other implants can also be useful.

Dose simulator 120 can also receive patient information from one or more peripheral devices 130. These peripheral devices 130 can provide information to dose simulator 120 by, for example, collecting information about a patient or about the imaging procedure. Non-limiting examples of peripheral devices that can be utilized include body scanner(s), camera(s), scale(s), and contrast injector(s). In one example, peripheral device 130 can be in the form of a body scanner 130a. Body scanner 130a can scan the patient's body to assess, for example, the patient's body size and/or shape (e.g., height, width, and other dimensions), convert these measurements to data, and transfer that data to dose simulator 120. In a variation of this example, peripheral device 130 can be in the form of a camera. The camera can capture an image of the patient (e.g., a full-length image of the patient), convert that image to data, and transfer that data to dose simulator 120 where it can be used to assess the patient's body size and/or shape (e.g., height, width, and other dimensions). In another non-limiting embodiment, peripheral device 130 can be in the form of a scale that captures a patient's weight, converts that weight to data, and transfers that data to dose simulator 120. Body scanners, cameras, and scales capable of performing these tasks are well known and commercially available.

Peripheral device 130 may also be a contrast injector 130b if, for example, the imaging procedure will involve the administration of contrast to the patient. Because the type and volume of contrast that will be present within the patient (as well as the location of that contrast within the patient at the time of the imaging procedure) can affect the radiation dose distribution within the patient, dose simulator 120 can use information about the contrast agent (including the type of contrast being used) and the administration of contrast (including the timing of the administration, volume of contrast, flow rate, etc.) when generating the patient-specific virtual radiation dose model. Dose simulator 120 can receive information from the contrast injector 130b concerning, for example, the type of contrast being used, the total volume of contrast being used, and the flow rate or other protocol parameters (including timing and/or phases).

Dose simulator 120 also receives scan data from imaging system 110. This scan data can be in the form of a data set from a limited (partial) imaging procedure of a patient. The scan data can include, for example, Hounsfield values for each measured voxel of the patient. To generate this scan data, a patient can be situated within imaging system 110, such as a CT scanner. The patient can then be subject to a limited imaging procedure that images at least a portion of the patient's body. In one non-limiting embodiment, the limited imaging procedure images only a portion of the patient's body, such as the torso and/or head. This can be done by selecting the appropriate region of interest for the scan, and subjecting the patient to the scan procedure in order to gather the scan data. By imaging only a portion of the patient's body, the total radiation (or other energy) exposure to the patient is reduced as compared to an imaging procedure that images a larger portion of the patient, or the patient's whole body. As will be described below, for purposes of dose estimation, areas of the patient's body not covered by the imaging procedure can be approximated using the patient information described above. In one non-limiting embodiment, a separate scout scan/localizer image can be gathered using imaging system 110 and the data generated during this scout scan/localizer image can be used by dose simulator 120 to approximate areas of the patient not subject to the limited imaging procedure described above.

Dose simulator 120 can receive information from imaging system 110, each peripheral device 130, and/or each information database 140 through a network connection, such as an Intranet, LAN, WAN, Bluetooth, or an Internet connection. By way of another example, some or all of this information can be stored in a cloud-based database accessible by dose simulator 120 through the Internet. Data transfer can be through wired or wireless means.

Based on the received patient information and scan data, dose simulator 120 can generate a patient-specific virtual radiation dose model of the patient. This dose model may be in the form of a three-dimensional (3D) voxel-based model. Dose simulator 120 can also use this dose model to perform a simulation/estimation of the dose received in a region of interest, and present a user with this dose information, such as a dose distribution, for the region of interest through a report generated by the dose simulator and/or by displaying such information on a graphical interface. The graphical interface may be a display 122 associated with dose simulator 120, as shown in FIG. 1, or it may be a display remote from dose simulator 120, such as a display at a radiologist's work station. Further details concerning the method of generating a patient-specific virtual radiation dose model of the patient, performing a simulation/estimation of the dose received in a region of interest, and presenting a user with this dose information are described below.

Figure 2:
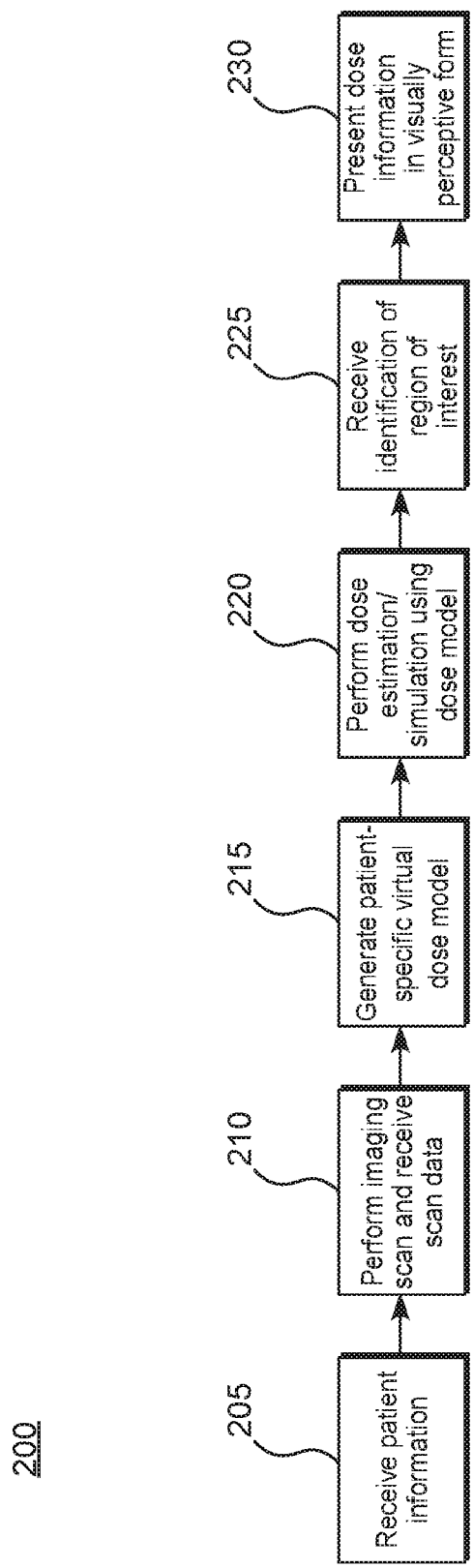
FIG. 2 illustrates a flow diagram of a method of estimating dose exposure in a region of interest according to one non-limiting embodiment of the present disclosure.

FIG. 2 illustrates a method 200 for operating dose simulator 120. As shown, the method 200 begins at step 205, where dose simulator 120 receives patient information. As described above, this information can include characteristics about the patient, such as the patient's age, height, body size, sex, weight, body mass index (BMI), and body shape. This information can be obtained from the various information sources described above, including the HIS, RIS, EMR, LIS, etc. as well as from one or more peripheral devices 130, such as the body camera, scale, body scanner, etc. The information can be automatically pushed to the dose simulator 120 when it is gathered, it can be requested and retrieved by dose simulator 120 using automatic data retrieval techniques, the information can be manually entered by a technician, or combinations thereof. For example, information obtained from a peripheral device 130, such as a body scanner, may be automatically sent to the dose simulator 120 once the information is gathered whereas information contained in the HIS, RIS, or EMR may be requested and retrieved by dose simulator 120. Data acquired during step 205 is transferred to dose simulator 120 using wired and/or wireless data transfer. Some or all of the patient information can be entered directly to dose simulator 120 through a user interface thereof.

In step 210 of FIG. 2, a limited (partial) imaging procedure of the patient is completed by imaging system 130. While step 210 is depicted as occurring after step 205, it can occur simultaneously with, or even before, step 205. As discussed above, the limited imaging procedure may image only a portion of the patient's body, such as the torso and/or head. This can be done by selecting the appropriate region of interest for the scan, and subjecting the patient to the scan procedure in order to gather the scan data. If desired, a separate scout scan/localizer image, such as a full body image, can be gathered using imaging system 110 and during step 210 as well. Data acquired during step 210 is then transferred to dose simulator 120 using wired and/or wireless data transfer.

At step 215, dose simulator 120 uses the patient information and scan data acquired in steps 205 and 210 to generate a patient-specific virtual dose model. In some non-limiting embodiments, the virtual dose model is a model of the full body of the patient. The virtual dose model can be generated by using the patient information and scan data to construct a 2D or 3D voxel-based model (e.g., a model formed of individual voxels) of the patient or a portion of the patient that includes tissue or other material (e.g., bone) assigned to each voxel so as to construct a model of the patient's body. This modeling process can involve extracting, from the scan data, the Hounsfield value attributed to each voxel of the patient that was imaged in step 210 and assigning a material or tissue type to each voxel based on the voxel's Hounsfield value. For example, dose simulator 120 can analyze the Hounsfield value for each voxel and, based on the value and known correlations between tissue/material type and Hounsfield value, determine the type of tissue(s) (e.g., liver, heart, etc.) or material(s) (e.g., bone, tendon, etc.) that are present in that voxel. Information on the known correlation between Hounsfield values and tissue/material type can be in the form of correlation data and can be stored in memory, such as in a database, that can be accessed by dose simulator 120 and can be based upon known correlations available in literature that would be available to a person of skill in the art.

As mentioned, the scan data obtained in step 210 may be only a partial scan of the patient whereas the desired dose model is a whole body model of the patient. To account for this, dose simulator 120 can estimate the material/tissue type for voxels of the patient in areas that are not covered by the scan data, such as areas that were not subject to the imaging procedure of step 210 or areas for which no Hounsfield information is contained in the scan data due to, for example, data corruption. This estimation can be accomplished using other information that is received in step 205 and/or step 210. This includes, for example, patient information of the patient's size, weight, or body shape obtained through manual entry, from one or more databases 140, and/or from one or more peripheral devices 130. For example, a body scanner or camera may obtain a full length photograph or body scan (2D or 3D) of the patient, a scale may obtain a patient's weight, or a body shape analyzing tool (e.g., Shapescale® from Shape Labs, Inc.; www.shapescale.com) may obtain a patient's body shape. From this information, dose simulator 120 can estimate the tissue or material type that would be present in each voxel. For example, if the scan data does not include data of an image of a patient's leg, a full length photograph of the patient may be used to determine the location and dimensions (e.g., length, thickness, etc.) of the patient's leg, including the components thereof (knee, shin, foot, ankle, etc.). Based on this location and dimension information, as well as on known information about the tissue/material that is typically present across different portions of a person's leg, the dose simulator 120 can assign tissues/materials to each voxel of the leg, thereby providing an estimate of the contents of these voxels even in the absence of scan data directed to these voxels. Similar estimations could be performed for other portions of the patient, such as the legs, lower torso, etc., so as to complete a whole body model of the patient, even without the benefit of complete scan data of the entire body.

In certain non-limiting embodiments, dose simulator 120 may use the available patient information, including the size, shape, and/or weight of the patient, to match the patient to an imaging phantom stored in a phantom database 150. Based on patient information, dose simulator 120 can query phantom database 150 to find a phantom that has characteristics that closely align with the characteristics of the subject patient. Alternatively, a user can select a particular phantom from phantom database 150 to use for the simulation. In yet another alternative, the patient information could be used to interpolate between imaging phantoms stored in phantom database 150 to build a 2D or 3D patient-specific phantom "on the fly" that can include at least the material/tissue type and/or density of the various voxels of the phantom. In each case, the selection process may additionally consider information about prior imaging procedures of the patient, such as whether a particular phantom was used with this patient in the past. This phantom could then be used to assign the material content of the voxels of the voxel-based patient model in voxel areas where insufficient scan data was obtained in step 210. This can be done, for example, by referencing the tissue density in certain voxels of the phantom and then using those tissue density measurements as an approximation of the tissue density in those same voxels (or at least similarly located voxels) of the patient. Matching of the voxel positions of the phantom to the voxel positions of the patient can be done using the known information about the patient's size/shape, and in some non-limiting embodiments, this matching can be done using the results of a localizers/scout scan of the patient. Methods of selecting phantoms from a phantom database are described, for example, in PCT Publication No. WO 2018/156803, entitled "Systems and Methods for Generating Simulated Computed Tomography (CT) Images" and assigned to Bayer Healthcare LLC, the entire contents of which are incorporated by reference herein.

Imaging phantoms are well known in the art and can be generally described as a model of the human body, or a portion thereof, that can be used in ionizing radiation studies in place of an actual human being. Virtual phantoms can provide accepted mathematical models of portions of human tissue, organs, structures, etc. For example, virtual phantoms may provide a set of non-uniform rational basis splines (NURBS) used to create a three-dimensional model of a human body (or portion thereof). Alternatively, the virtual phantoms may be represented using constructive solid geometry (CSG) or other mathematical representation. Examples of suitable virtual phantoms include volumetric (voxel) or surface based (mesh or NURBS) phantoms. Such phantoms can be created by loading organs into the computer memory individually as non-intersecting closed volumes. The organs are organized in a hierarchy based on which organs are enclosed within which (e.g., brain is contained in skull). The hierarchy of organs on the basis of encompassment is necessary for determining the traversed lengths by each ray within organs. Next, tissue material and densities (as described by ICRP or NIST tables) are assigned to organ volumes, e.g., bone material to bones, soft tissue to muscles, and so on. This may be done automatically based on the organ names but a user would have the option to modify the automatic assignment of tissue materials and densities to suit his or her needs.

Phantom database 150 can be pre-populated with a set of available imaging phantoms that have been previously created. Additional phantoms can be added to phantom database 150 when they are created. The phantoms in phantom database 150 can also be periodically updated or adjusted by modifying the particular characteristics of the phantoms based on, for example, additional information that is learned about the accuracy or performance of the phantom. Phantom database 150, as well as dose simulator 120 (or aspects thereof), may be remote and cloud based. For example, aspects of dose simulator 120 configured to generate a virtual phantom may be cloud based and remote from scanning environment 100 or portions thereof (e.g., imaging system 110) whereas other aspects of dose simulator 120 may be co-located with scanning environment 100 or the components thereof.

The phantom may be deformed to better align the characteristics of the phantom with the subject patient, including BMI, height, gender, and other anatomical metrics. In one non-limiting embodiment, the phantom can be modified to better align the tissue and/or bone density representations of the phantom with known tissue and/or bone density information of the subject patient. For example, a patient diagnosed with osteoporosis would have a lower bone density. The tissue material and density affect the attenuation of the x-ray beam as it passes through the phantom organs during the simulation. In another non-limiting embodiment, other details such as a pacemaker and metallic or other implants can also be incorporated into the phantom. If the phantom has a circulatory system, the user can specify at this point if a contrast material is present and set the related parameters. In non-limiting embodiments, a virtual phantom can be deformed using the techniques described in U.S. Pat. Nos. 8,958,617 and 9,547,893 and U.S. Patent Application Publication Nos. 2017/0228860 and 2017/0243350, the contents of which are incorporated herein by reference. Suitable deformations include adjusting the shape of the organs and adjusting the tissue densities using information about the subject patient, such as existing images of the patient.

In cases where contrast is used, the virtual dose model of the patient may be modified to incorporate the contrast agent into certain voxels based on, for example, information obtained from a contrast injector in step 205. As discussed above, this information can include the type of contrast being used, the total volume of contrast being used, and the flow rate or other protocol parameters (including timing and/or phases). If it is determined that contrast was (or would be) present in a particular voxel of the patient, the material/tissue assigned to that voxel can be adjusted to account for the presence of contrast in that material/tissue. This adjustment can be done based on a known Hounsfield value associated with the contrast agent in conjunction with other available information on the contrast, including contrast dosage, such as the type of contrast and volume of contrast. This information could be obtained from, for example, a contrast injector 130b in communication with dose simulator 120 or it may be supplied by a technician, such as through manual entry.

As an outcome of step 215, dose simulator 120 can generate a patient-specific virtual radiation dose model based on patient information received in step 205 and the scan data from the partial imaging procedure obtained in step 210, subject to various modifications and adjustments, including those discussed above. This patient-specific virtual radiation dose model can be a whole body model of the patient (e.g., a model of the patient's entire body) and can be a voxel-based model in which the content of each voxel of the patient is determined based on the measured or estimated material/tissue/contrast agent present in that voxel, as explained above.

With reference to step 220 of FIG. 2, once the virtual dose model is constructed, it can be used as an input to a dose calculation program to calculate an estimated dose or exposure delivered to a patient. In certain non-limiting embodiments, dose simulator 120 is capable of determining this dose or exposure information on a voxel-by-voxel basis. Dose simulator 120 can provide a user with the flexibility to define a region(s) of interest (such as through the selection of certain voxels) for which dose information is desired.

In certain non-limiting embodiments, dose estimation can be accomplished using one or more known Monte Carlo simulation techniques, such as those discussed in U.S. Pat. Nos. 8,953,861 and 9,792,680 and United States Patent Application Publication Nos. 2017/0123074 and 2017/0228860, which are expressly incorporated herein by reference. These Monte Carlo simulation techniques can estimate the dose absorbed in a particular portion of the patient, such as on a voxel-by-voxel basis or by grouping together nearby voxels having similar material content. Such simulation techniques can use the patient-specific virtual radiation dose model developed in step 215, along with a number of settings related to imaging system 110 and procedure to be performed, in order to compute accurate estimates of radiation dose. For example, if imaging system 110 is a CT scanner, the scanner may be modeled for purposes of the simulation using parameters such as kVp, i.e., peak kilovoltage, X-ray generator target angle, fan angle, collimation, slice thickness, focus to axis distance, flat filters (material and thickness), and beam shaping filters (material and geometry). Spectral data, energy spectrum data, and a model of the effect of beam hardening can also be considered to improve the accuracy of the simulation. For example, sensors in the scanner bed can be used to measure the photon spectra, or data can be derived from scans of density calibration phantoms. Of course, these (and other parameters) may be selected as available or as needed to suit the needs of a particular case.

Dose simulator 120 can carry out the simulations to estimate the dose delivered to each voxel of the virtual dose model from the imaging procedure. Dose can be determined on the basis of energy per mass. In some non-limiting embodiments, the patient could instead be matched to the closest phantom in the phantom library (discussed above), and the dose estimates could be taken from stored results of previous simulations that used this phantom or interpolated from results of similar phantoms.

In certain non-limiting embodiments, the simulation can also incorporate other objects that may be in the room, including persons other than the patient and equipment. For example, if a technician wearing a shielded apron is standing next to the patient, radiation scattered from the technician and apron could contribute to the dose received by the patient. Similarly, if other equipment is present in the room with the patient, radiation scattered from this equipment could contribute to the dose received by the patient. The dose simulation can estimate the dose incident or received by the other person(s) or equipment and can also estimate any additional dose delivered to the patient caused by the scattering radiation. The location, size, and position of the objects in the room can be modeled using data obtained by 3D scanners or cameras present in the room that capture the location, size, and position of these objects. In some non-limiting embodiments, the location, size, and position of these objects could be gathered prior to or at the beginning of the scan. This information, or at least the positioning information, could be updated in real time throughout the scan to account for movement of the objects during the scan, and this updated information can then be used in generating dose calculations that reflect the movement of objects over time. Dose simulator 120 can use this information to provide general estimations of the dose received by persons other than the patient, and how the dose rates for all persons in the room evolve over time can be calculated, recorded and/or reported.

With reference to step 225 of FIG. 2, a user can select one or more regions of interest and receive dose information, such as a dose distribution or an average dose (e.g., mGy), within the selected region(s) of interest. While step 225 is shown as occurring after step 220, it could occur simultaneously with, or even before, step 220, in which case the defined region of interest could dictate the area for which the dose simulation is performed. A graphical interface, such as a touchscreen display, can be used to allow the user to select the region(s) of interest. This selection process can proceed in a number of ways. In one non-limiting example, the user can select voxels on a slice-by-slice basis, such as by drawing a 2D geometric (e.g., circular or rectangular) or freehand shape on each slice, or use the interface to draw a geometric volume in three dimensions. In another non-limiting example, dose simulator 120 can identify/segment organs automatically, such as by grouping together nearby voxels having the same or similar assigned material/tissue content, and then suggest these organs as possible regions of interest to the user, with the user being able to augment or reduce the suggested regions as needed. In another non-limiting example, dose simulator 120 can identify the boundaries of the irradiated region using information from the scanner/device, and include tools to limit the regions of interest to these boundaries.

With reference to step 230, dose information can be compiled and presented to the user in a variety of formats.

Figure 3:
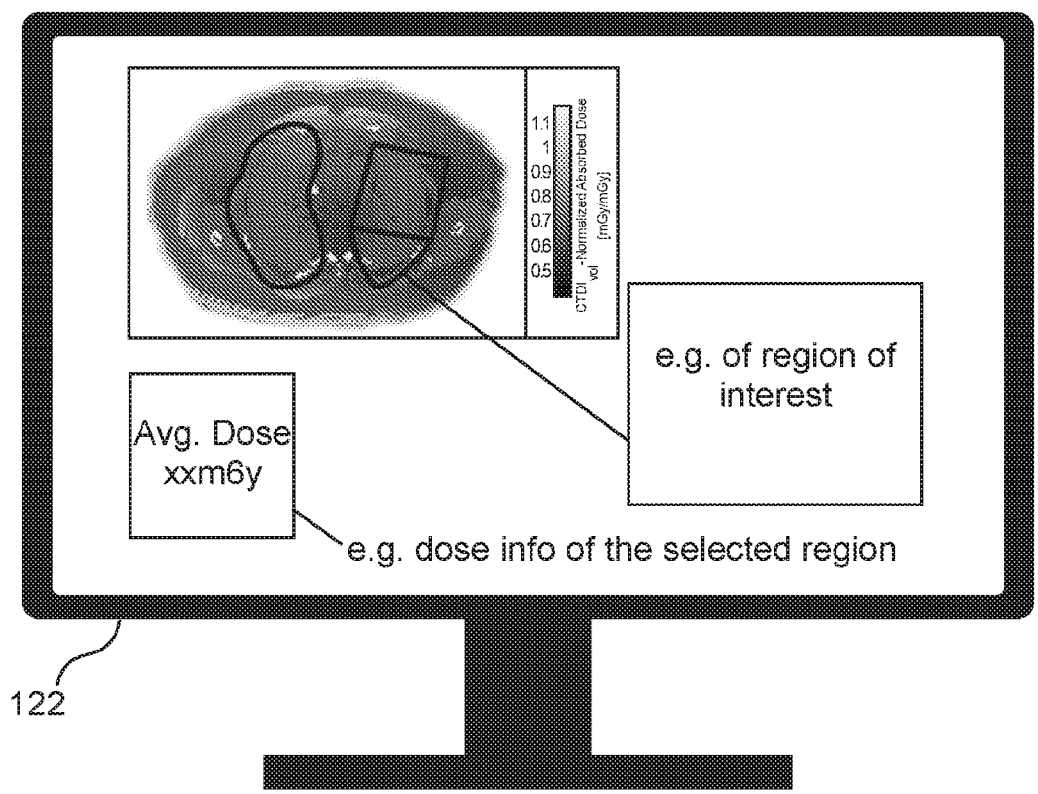
FIG. 3 illustrates a depiction of a display for reporting dose exposure information according to one non-limiting embodiment of the present disclosure.

For example, in one non-limiting embodiment, as the regions of interest are defined, the dose simulator 120 can display information on the dose distribution to the user, such as through a graphical interface/display 122 associated with dose simulator 120. The displayed information can include quantities, such as the total dose in the region, the standard deviation of the per-voxel doses in the region, or other statistics that may be of interest. A histogram of the per-voxel dose distribution can be displayed for each region. In certain non-limiting embodiments, dose information could also be visualized as a color-coded "heat map" on a slice by slice basis, or as a series of transparent dose contour surfaces in three dimensions. FIG. 3 presents an example of dose information, including a heat map, displayed on a display 122 according to one non-limiting embodiment.

Dose information can also be collected into a report that can be presented to the user and/or stored in a database for future use and review. For example, the dose information could be used to create a report on the cumulative patient radiation dose received over the course of multiple imaging procedures for a given patient, which tracks the dose delivered to the patient. Because, in certain embodiments, the patient-specific virtual radiation dose model is a full body model of the patient, this report can track the total dose received by the patient. If a report has already been created for the patient, it could be updated to include the dose information from subsequent procedures. The dose information could be made available to the patient's doctors and other staff (such as radiologists, scan technicians, medical physicists, or radiation therapy professionals) at the site, and also to the patient (if desired). This information can also be exported to a dose registry which may be contained in one or more databases.

The dose information generated through the methods described in the present disclosure can be used to assess the patient's risk of developing certain conditions (such as organ specific cancers, or cataracts if the eye lenses are irradiated). If information exists in the patient history to indicate increased (or decreased) susceptibility to developing given conditions, this information could be incorporated into the risk estimates of those conditions for the patient.

In certain non-limiting embodiments, the dose information can also be used to predict radiation dose for future diagnostic imaging. For example, dose information for a given patient and imaging procedure can be stored in a database. If that patient returns for a future diagnostic imaging procedure, the dose information from the prior procedure can be retrieved and the patient information and procedure information from that prior procedure can be compared to the current patient information and procedure. If the patient information and procedure information are substantially the same, the prior dose information can be a good predictor of the dose exposure for the current procedure. This process is not limited to only procedures involving the same patient. Dose information from prior procedures of a patient may also be a good predictor for future diagnostic imaging of a different patient if, for example, the patient information (e.g., size, sex, body shape) between the prior and current patients is comparable.

An exemplary procedure according to certain non-limiting embodiments of the present disclosure could include at least the following steps: (1) data about the patient and the procedure are input or otherwise received by dose simulator 120, including at least patient size, patient shape, patient weight, the presence of contrast media, and scan protocol information including injection and imaging timing; (2) conduct one or more partial CT scans of a portion of the patient and obtain the scan data from the scanner; (3) extract the Hounsfield units per pixel from the acquired scan data; (4) create a 2D or 3D patient-specific, material voxel-based virtual model of the patient including tissue density; (5) for portions of the patient's body for which scan data is not available, fill in the virtual model using additional patient information, such as size or weight; (6) input the patient-specific virtual model to a Monte Carlo dose simulator; (7) select a region of interest, such as a segment, from within the virtual model; and (8) using desired inputs, calculate an estimate of the radiation dose over the region of interest.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:

1. A system, comprising:
a dose simulator in communication with an imaging system, the dose simulator comprising a user interface, a processor, and a non-transitory storage medium comprising programming instructions,
wherein the programming instructions, if executed, enable the processor to cause the dose simulator to:
receive patient information about the patient, wherein the patient information comprises information about one or more physical characteristics of the patient;
receive scan data, wherein the scan data is generated during an imaging scan of the patient by the imaging system, wherein the imaging scan is a partial imaging scan of a portion of the patient, and wherein the scan data represents partial scan data covering the portion of the patient;
create a virtual dose model of the patient based upon the patient information and the partial scan data;
receive a selection of a region of interest of the patient;
perform a dose simulation on the virtual dose model of the patient or a portion thereof; and
determine, based upon an outcome of the dose simulation, an estimate of the radiation dose received within the region of interest.

2. The system of claim 1, wherein the programming instructions, if executed, further enable the processor to present the estimate of the radiation dose received within the region of interest in a visually perceptible form on a display screen.

3. The system of claim 1, wherein the patient information comprises at least one of a height, a body size, a body weight, and a body shape.

4. The system of claim 1, further comprising a peripheral device, wherein at least a portion of the patient information is received from the peripheral device.

5. The system of claim 4, wherein the peripheral device is selected from the group consisting of a body scanner, camera, scale, and contrast injector.

6. The system of claim 1, wherein the virtual dose model comprises a plurality of voxels, wherein a material or tissue type is assigned to each of the plurality of voxels.

7. The system of claim 1, wherein the virtual dose model is a full body model of the patient.

8. The system of claim 1, wherein the dose simulation is performed on the virtual dose model through the use of a Monte Carlo simulation technique.

9. The system of claim 1, wherein the imaging system is a computed tomography system and the imaging scan is a computed tomography scan.

10. Dose simulator software stored on a non-transitory storage medium to providing an estimate of radiation dose received by a patient during an imaging scan performed by an imaging system, the software comprising programming instructions that, if executed, enable a processor to cause the dose simulator software to:
receive patient information about the patient, wherein the patient information comprises information about one or more physical characteristics of the patient;
receive scan data, wherein the scan data is generated during an imaging scan of the patient by the imaging system, wherein the imaging scan is a partial imaging scan of a portion of the patient, and wherein the scan data represents partial scan data covering the portion of the patient;
create a virtual dose model of the patient based upon the patient information and the partial scan data;
receive a selection of a region of interest of the patient;
perform a dose simulation on the virtual dose model of the patient or a portion thereof; and
determine, based upon an outcome of the dose simulation, an estimate of the radiation dose received within the region of interest.

11. The dose simulator software of claim 10, wherein the programming instructions, if executed, further enable the processor to present the estimate of the radiation dose received within the region of interest in a visually perceptible form.

12. The dose simulator software of claim 10, wherein the patient information comprises at least one of the patient's height, body size, body weight, and body shape.

13. The dose simulator software of claim 10, wherein the virtual dose model comprises a plurality of voxels, wherein a material or tissue type is assigned to each of the plurality of voxels.

14. The dose simulator software of claim 10, wherein the virtual dose model is a full body model of the patient.

15. The dose simulator software of claim 10, wherein the dose simulation is performed on the virtual dose model through the use of a Monte Carlo simulation technique.

16. A method of providing an estimate of radiation dose received by a patient during an imaging scan performed by an imaging system, comprising:
receiving patient information about the patient, wherein the patient information comprises information about one or more physical characteristics of the patient;
receiving scan data, wherein the scan data is generated during the imaging scan of the patient by the imaging system, wherein the imaging scan is a partial imaging scan of a portion of the patient, and wherein the scan data represents partial scan data covering the portion of the patient;
creating a virtual dose model of the patient based upon the patient information and the partial scan data;
receiving a selection of a region of interest of the patient;
performing a dose simulation on the virtual dose model of the patient or a portion thereof; and
determining, based upon an outcome of the dose simulation, an estimate of the radiation dose received within the region of interest.

17. The method of claim 16, wherein the patient information comprises at least one of a height, a body size, a body weight, and a body shape.

18. The method of claim 16, wherein at least a portion of the patient information is received from a peripheral device selected from the group consisting of a body scanner, camera, scale, and contrast injector.

19. The method of claim 16, wherein the virtual dose model comprises a plurality of voxels, and wherein creating a virtual dose model comprises assigning a material or tissue type to each of the plurality of voxels.

20. The method of claim 19 wherein assigning the material or tissue type to each of the plurality of voxels comprises, for each of at least a portion of the plurality of voxels, extracting from the scan data a Hounsfield value attributed to the voxel and comparing the Hounsfield value of the voxel to correlation data representing a known relationship between Hounsfield values and types of materials or tissues.

21. The method of claim 20 wherein assigning the material or tissue type to each of the plurality of voxels comprises accounting a presence of a contrast agent in one or more of the voxels.

22. The method of claim 16, wherein the virtual dose model is a full body model of the patient.

23. The method of claim 22 wherein creating the virtual dose model comprises determining a plurality of voxels for which no scan data is available and assigning a material or tissue type to each of the plurality of voxels for which no scan data is available by using the patient information to estimate the material or tissue type in the plurality of voxels for which no scan data is available.

24. The method of claim 23 wherein assigning a material or tissue type to each of the plurality of voxels for which no scan data is available further comprises accessing a phantom database and referencing a tissue or material type in a corresponding voxel of a phantom selected from the phantom database.

25. The method of claim 16, further comprising:
obtaining information of a location, size, and position of one or more objects other than the patient; and
updating the dose simulation of the virtual dose model to account for radiation scattered from the one or more objects other than the patient.

* * * * *